United States Patent [19]

Pappas et al.

[11] Patent Number: 5,074,879
[45] Date of Patent: Dec. 24, 1991

[54] PROSTHETIC DEVICE WITH MODULAR STEM

[76] Inventors: Michael J. Pappas, 61 Gould Pl., Caldwell, N.J. 07006; Frederick F. Buechel, 76 Crest Dr., South Orange, N.J. 07079

[21] Appl. No.: 601,651

[22] Filed: Oct. 26, 1990

[51] Int. Cl.⁵ .................................................. A61F 2/32
[52] U.S. Cl. .......................................... 623/18; 623/23
[58] Field of Search ..................... 623/16, 18, 19, 20, 623/23

[56] References Cited

U.S. PATENT DOCUMENTS 4,520,511 6/1985 Gianezio et al. ...................... 623/23

FOREIGN PATENT DOCUMENTS

| 0243298 | 4/1987 | European Pat. Off. |
| 0290735 | 3/1988 | European Pat. Off. |
| 0325407 | 1/1989 | European Pat. Off. |
| 0382429 | 8/1990 | European Pat. Off. ............... 623/23 |
| 7834900 | 6/1987 | Fed. Rep. of Germany. |
| 2616060 | 3/1979 | France. |

Primary Examiner—David J. Isabella
Attorney, Agent, or Firm—Anthony J. Casella; Gerald E. Hespos

[57] ABSTRACT

A modular stem type prosthesis is provided which includes a stem and an extension which are connected to one another with a slip fit interconnection that minimizes surface tensile forces in regions of the prosthesis adjacent the interface between the stem and the extension. Engagement between the stem and the extension is provided by deflectable end portions of one component of the prosthesis which are engaged in a mating deformation in the other component. The mating structures may define an interfitting ridge and groove. Micromotion between the respective parts may be prevents by a screw which may be tapered to achieve a lock fit. The extension may be of any selected length and any selected diameter in accordance with the needs of the patient.

10 Claims, 6 Drawing Sheets

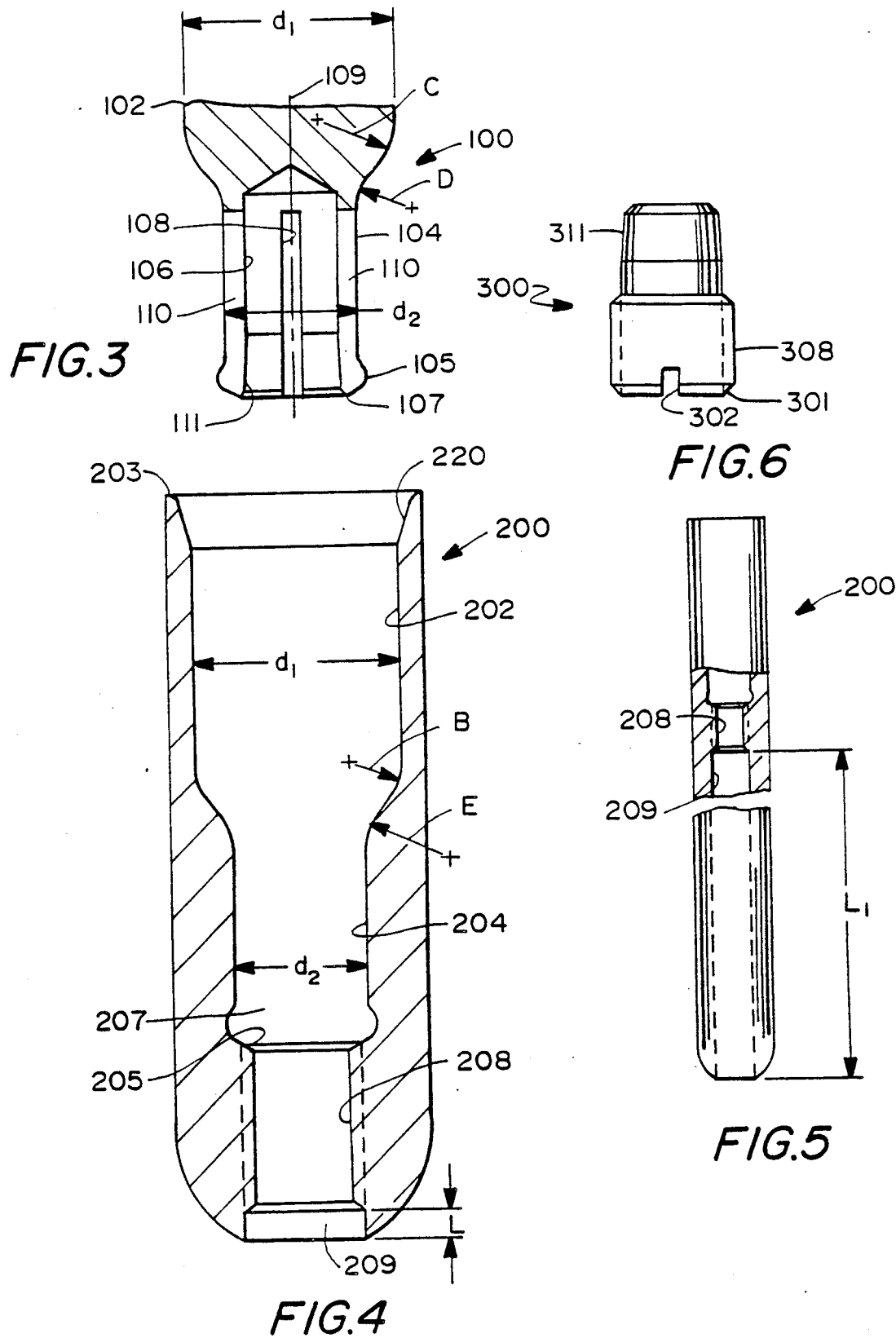

PROSTHETIC DEVICE WITH MODULAR STEM

BACKGROUND OF THE INVENTION

A stem type femoral hip replacement prosthesis comprises an elongated stem for placement in the intramedullary cavity of the femur and a head defining the proximal end of the prosthesis for replacing proximal portions of the natural femur. The head of the prostheses is substantially spherical and is pivotally engageable in an acetabular cup which defines a separate portion of a prosthetic system which is affixed to the natural acetabular. The stem type femoral prosthesis may further include a collar for engagement against the resected proximal end of the natural femur, and a neck extending from the collar to the head. Most prior art stem type femoral prostheses have been of unitary construction. However many prior art stem type prostheses have been of modular construction with any of a plurality of heads being selectively engageable on any of a plurality of necks. The particular head and neck combination has been selected to achieve optimum fit in the patient. Examples of prior art femoral stem type prostheses are shown in U.S. Pat. No. 4,752,296 which issued to the inventors herein on June 21, 1988.

The best length and diameter of the stem of a stem type femoral hip replacement prostheses is dependent on the patient's physiology and pathology. For example, a small patient with considerable disuse atrophy of the femur may have a wide intramedullary cavity or femoral canal and thus may require a prostheses with a small proximal end but a large stem diameter for proper fit in the intramedullary cavity of the femur. In other instances, an extra long stem may be needed to span a femoral fracture or other defect, and thus allow the prosthesis to act as a support for the defect while healing occurs.

Typically the prosthesis, and particularly the stem of the prosthesis, have been custom made to accommodate the specific physiological and pathological needs of the patient. This typical prior art approach has at least three major disadvantages. In particular: the custom made prosthesis is very expensive; there is considerable time required to obtain the prosthesis, during which time the patient can be adversely affected; and, fitting the prosthesis from x-ray data is not completely reliable, and the custom made prosthesis may in fact not fit well, if at all.

In view of the preceding problems, some prior art prostheses have been developed with modular stems to alter the length of the stem in accordance with the particular needs of the patient. A stem extension of a selected length can be added to the proximal portion of the stem type prosthesis to allow fitting intraoperatively. These prior art modular stem prostheses generally have employed a conical taper fit between the proximal portion of the prosthesis and the extension. Some such prior art modular stem type prostheses have employed a screw to force the mating tapered ends tightly together.

The interengagement of the mating male and female tapered components of the prior art modular stem type prosthesis produces substantial tension forces on the surface of the female component. More particularly, the forceful urging of the component having the male taper into the component having the female taper urges the female tapered portion outwardly to generate the substantial tension forces on the surface of that member. These substantial tensile forces necessarily occur at critical surface areas near the stem-extension interface. The tension forces developed in this context can be compared to the hoop stresses created on the hoops of a barrel. Unlike a barrel, however, the prothesis is repeatedly subjected to bending stresses during normal usage. During instances of such bending stress, the portion of the prothesis having the female taper will be subjected to complex tension forces caused both by the wedging action of the mating tapers (e.g., hoop stress) and by the bending stresses. Such surface tensile stresses are highly undesirable in that they contribute substantially to fatigue of the prosthesis, and thus substantially weaken the stem/extension composite structure at the structurally critical interface of the stem and the stem extension. In particular, microfissures or microcracks in the surface of the component having the concave taper can experience accelerated propagation when subjected to additional tensile forces in response to the bending stresses exerted on these critical regions of the prostheses during normal usage.

In view of the above, it is an object of the subject invention to provide a modular prosthesis that enable optimum fitting to the patient.

It is another object of the subject invention to provide a modular prosthesis that reduces tensile forces significantly in critical areas of the prosthesis.

It is a further object of the subject invention to provide a modular prosthesis having a stem and a stem extension which minimize tensile forces at surface regions adjacent the interface of the stem and the extension of the prostheses.

SUMMARY OF THE INVENTION

The subject invention is directed to a modular stem type prosthesis that does not include or require wedging or tapered interfit of parts at surface regions adjacent to the interface of those parts. The prosthesis of the subject invention comprises a stem and an extension. The extension has a length selected in accordance with the physiology and pathology of the patient. The diameter of the stem extension also is selected in accordance with the physiology and pathology of the patient. The diameter of the extension ma exceed the diameter of the stem to which the extension is mated. In a typical embodiment, the stem may define the proximal end of the prosthesis, while the extension defines the distal end. The prosthesis may be a stem type femoral prosthesis which may further comprise a collar, a neck and a head.

The stem of the prosthesis and the extension rely substantially upon a "slip fit" interengagement therebetween. In this context, "slip fit" is a term of art commonly used in machine tool technology to define a accurate interfit relying substantially upon close sliding telescoped interengagement substantially free of force fitting and/or wedge fitting and free of excessive play. One component of the modular prosthesis may comprise a plurality of longitudinally extending deflectable fingers which may terminate in enlarged arcuately extending ridges. The other component of the modular prosthesis may include a cavity into which the first component extends. The cavity may be provided with an outwardly extending arcuate groove for receiving the ridges at the ends of the deflectable fingers. The relative dimensions of the components may be selected to require an initial inward deflection of the fingers as the ridges approach the groove. The fingers may then resiliently return toward their undeflected condition such that the ridges of one component engage in the groove of the other component.

The modular prosthesis system of the subject invention may further include a screw which is engageable into one of the two interengaged components for securely retaining the ridges of the one component in the grooves of the other component. The screw may be tapered along its length to effectively lock the screw into one or both members and prevent unintended threaded separation therefrom. The tapering of the screw can further ensure the locked engagement of the ridges in the groove. Although this tapering may achieve some wedging action, the wedging forces are less than on conventional designs and are substantially spaced from the critical surface regions at the interface of the two components, and therefor does not create the problems of tension forces on the surface caused by the wedging interfit of the tapered members.

BRIEF DESCRIPTION OF THE DRAWINGS

FIG. 3 is a cross-sectional view taken along line 3—3 in FIG. 2.

FIG. 4 is a cross-sectional view of a stem extension of the modular prosthesis.

FIG. 5 is a side elevational view, partly in section, of an alternate extension.

FIG. 6 is side elevational view of a locking screw for use with the stem and stem extension of FIGS. 2-4.

DETAILED DESCRIPTION OF THE PREFERRED EMBODIMENT

Figure 1:
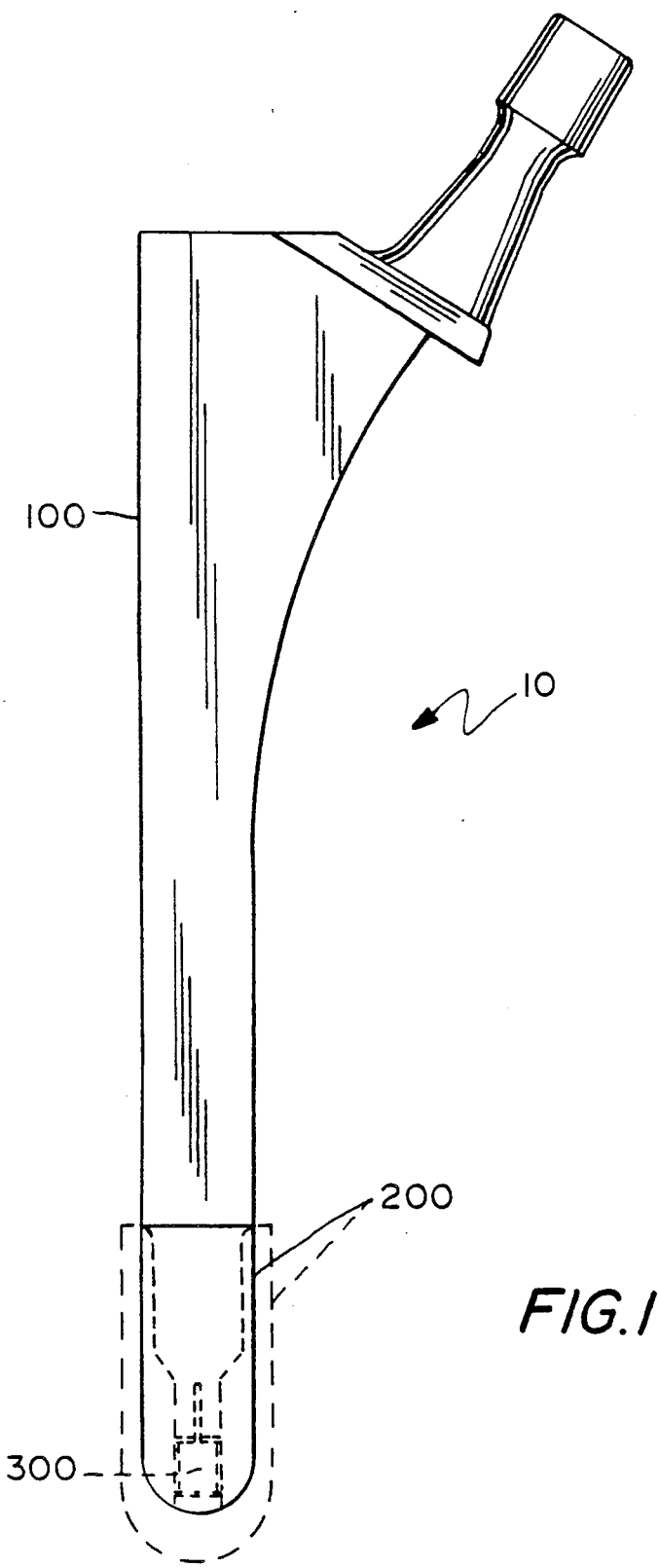
FIG. 1 is a front elevational view of a modular prosthesis in accordance with the subject invention.
Figure 2:
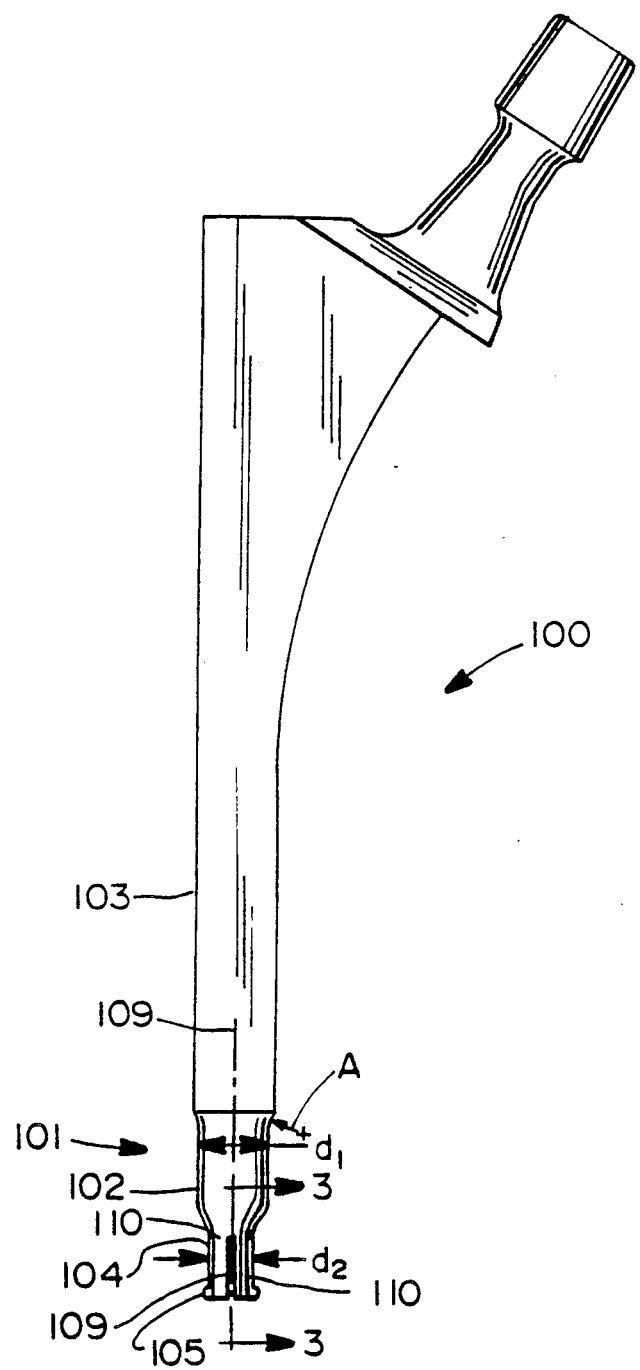
FIG. 2 is a front elevational view of the stem portion of the modular prosthesis.

A femoral stem 100 type prosthesis in accordance with the subject invention is identified generally by the numeral 10 in FIG. 1. The prosthesis 10 comprises a stem 100, an extension 200 and a locking screw 300. Referring to FIGS. 2 and 3, the stem 100 includes an end portion 101 which comprises a first cylindrical section 102 of diameter $d_1$ which joins an intermediate portion 103 of the stem 100 in a large radius A. This junction of the first cylindrical section 102 and the intermediate portion 103 of the stem 100 is the critical stress area for stem bending, which is the major contributing factor to stem breakage problems. The first cylindrical section 102 of the stem 100 joins with a second cylindrical section 104 of diameter $d_2$ through generous fillet radii C and D a shown in FIG. 3. The end of the second cylindrical section 104 is defined by a circular ridge 105. A hole 106, which terminates in taper 111, is drilled or bored in the end 107 of the stem 100 and four slots 108 are made in the second cylindrical section 104 running parallel to the axis 109 of femoral stem 100 dividing the second cylindrical section 104 into four flexible segments 110.

Turning to FIGS. 4 and 5, the extension 200 with axis 201 has a first extension cylindrical section 202 approximately of diameter $d_1$, which mates with the corresponding first cylindrical section 102 of the femoral stem 100. The first extension cylindrical section 202 has a chamfer 220 at its entrance 203. A second extension cylindrical section 204 approximately of diameter $d_2$ is disposed to mate with the second cylindrical section 104 of the femoral stem 100. The first extension cylindrical section 202 is joined to the second extension cylindrical section 204 by generous fillet radii B and E. The inner end 207 of the second extension cylindrical section 204 terminates in a circular groove 205 which is disposed to mate with the corresponding circular ridge 105 in the femoral stem 100. Adjacent to circular groove 205 of the extension 200 is a threaded hole 208 and a guide hole 209. The threaded hole 208 will be substantially the same length for extensions in a system of prostheses 10. However, the length L of the guide hole 209 will be a function of the length of the extension 200. As shown in FIG. 5, the extension 200 may be made in various lengths or outside diameter the smallest of which would be equal to the outside diameter of the femoral stem 100.

With reference to FIG. 6 a locking screw 300 is used to help hold the femoral stem 100 and the extension 200 together. The locking screw 300 consists of a tapered end 311 which mates with the taper 111 of femoral stem 100, and a threaded section 308 which mates with threaded hole 208 of the extension 200. The screw end 301 contains a slot 302 or other detail for turning the screw with a screw driver or other tool.

In use the surgeon selects a femoral stem 100 size appropriate to the size of the patient's proximal femur and selects an extension diameter and length appropriate for the patient's femoral shaft or intramedullary cavity. The end portion 101 of the femoral stem 100 is inserted in the entrance 203 of the extension 200 until the leading edge 112 of the circular ridge 105 engages radius E leading into the second extension cylindrical section 204. Further insertion causes deflection of the four flexible segments 110 inwardly so that they can pass through the second extension cylindrical section 204 until the circular ridge portions 105 of the four flexible segments 110 are in the circular groove 205 where they expand outwardly retaining the extension 200 on the femoral stem 100. The tapered end 311 of the locking screw 300 is then inserted in the guide hole 209 of the extension 200 until the threaded hole 208 in extension 200 engages the threaded section 308 of the locking screw 300. A screw driver, or similar tool is then used to turn the locking screw 300 until tapered end 311 of the screw 300 engages taper 111 of the femoral stem 100. Further turning of the locking screw 300 will cause outward deflection of the four flexible segments 110 such that the circular ridge portions 105 thereof are urged tightly into the circular groove 205 firmly holding extension 200 to the femoral stem 100. Further the effect of the wedge fit produced by taper 111 and tapered end 311 lock the screw 300 against loosening.

It will be noted that the prosthesis 10 uses a taper and screw to hold the extension 200 to femoral stem 100. However, unlike earlier devices the taper-screw connection is a smaller secondary connection and as such produces relatively small surface tensile stresses on the outside of the extension. Furthermore, and importantly, any minor effect of this taper and screw connection is away from the critical stress regions near radii A and B in the femoral stem 100 and the extension 200 respectively. The primary connection is a cylindrical slip fit between the first cylindrical section 102 and the first extension cylindrical section 202, with the slip fit being free of significant assembly stresses. Further, the taper 111 at the end 107 of the stem 100 and the tapered end 311 of the locking screw 300 need not be very accurately made in order to function properly while a primary taper connection, as in the prior art, requires very accurately tapered surfaces.

A further advantage of the prosthesis 10 is that the locking screw 300 is not strictly needed to hold the stem 100 and the extension 200 together since they are held together by the detent action of the ridges 105 of the four flexible segments 110 in the circular groove 205 of the extension 200. Thus in the unlikely event of the secondary taper connection failure, the femoral stem 100 and extension 200 would remain assembled. If a primary taper connection fails the parts will separate. The primary reason for the secondary connection provided by the screw 300 is to avoid micromotion between femoral stem 100 and extension 200, and thus to avoid metallic wear products of such motion.

The relative diametrical dimensions of the stem 100 and the extension 200 in regions of the slip fit therebetween should be selected to achieve optimum strength for the prosthesis 10 in response to bending stresses exerted thereon. For example a large diameter of the first cylindrical section 102 of the stem 100 could provide a small radial thickness of the first extension cylindrical second 202 with failure of the extension 200 in response to bending stresses being possible. Conversely, a radially thicker extension 200 could yield a stem 100 that is possible to fail in response to bending stresses exerted thereon. The relative dimensions should be selected to achieve a balanced design where the stem 100 and the extension 200 contribute equally to the strength of the prosthesis 10 in response to bending stresses. The optimum relative dimensions can be derived from the calculations set forth below.

The basic assumption for these calculations is that simple bending equations for shafts are adequate for this case. Thus assumption is clearly conservative. The stem 100 and extension 200 can only see stresses resulting from bending loads and much lower stresses from possible compressive loads on the end of the extension 200. Ignoring compression loads is conservative since this load reduces the tension bending stress component which produces fatigue failure.

Figure 7:
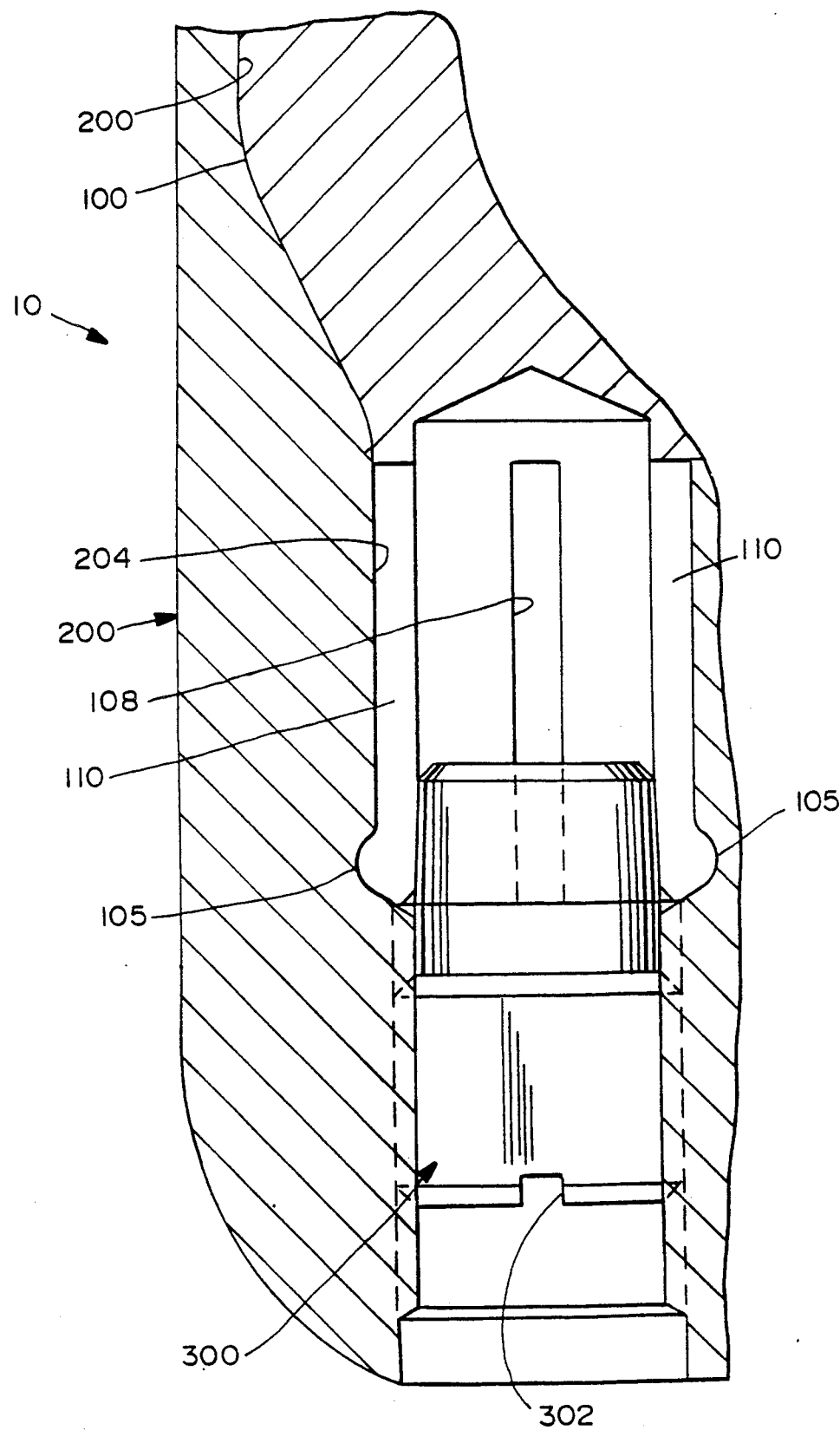
FIG. 7 is a cross-sectional view taken along line 7—7 in FIG. 1.
Figure 8:
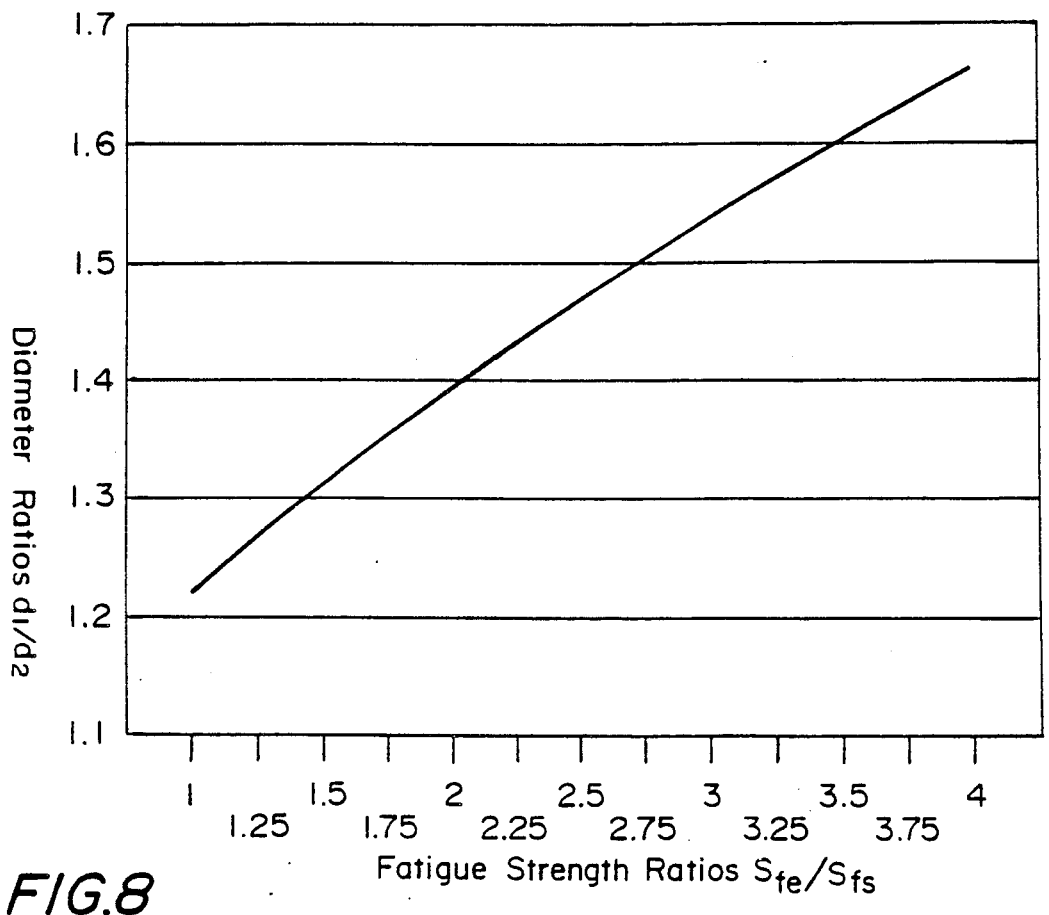
FIG. 8 is a graph showing the relationship of diameter to fatigue strength ratios.
Figure 9:
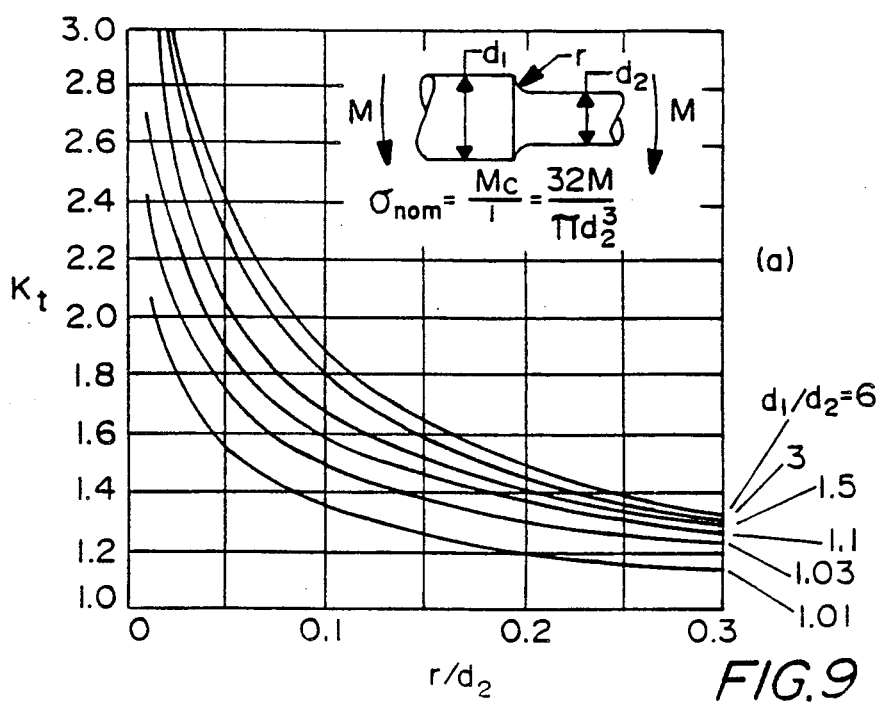
FIG. 9 is a graph showing the relationship of stem geometry to stress concentration.

Referring to FIGS. 2-4 it will be appreciated that the critical region for stress in the stem 100 is at radius A and for the extension at radius B. A balanced design in which the stress becomes critical in both parts may be found from FIGS. 6 and 7 and from Eq. 1.

$$S_{fe}/S_{fs} = (K_e/K_s)[(d_1/d_2)^3 - d_2/d_1] \quad (1)$$

where $S_{fs}$, $S_{fe}$, $K_e$, and $K_s$ are the fatigue strength and the stress concentration factors of the stem and extension respectively, and M in FIG. 7 is the bending moment applied to the assembled stem and extension. The diameters $d_1$ and $d_2$ are as given in FIGS. 2, 4 and 7. The indicated calculations are obtained by noting that both parts are critically loaded when the stress in each is equal to its fatigue strength and that the bending moment in each is the same.

The stress concentration factor is a function of $d_1/d_2$ from FIG. 7, which is drawn from *Machine Design Theory and Practice*, by Deutschman et al. The stress concentration factor in the stem is assumed equal to the stress concentration factor in the extension for these calculations. This assumption is made reasonable by making radius A larger than B for the stem design. Values of $d_1/d_2$ as a function of the ratio of the fatigue strengths using this assumption are given in FIG. 6.

The strength of an extended stem two-piece stem may be compared to a conventional unitary stem by Eq. 2.

$$R = [S_{fe}/(S_{fs}K_e)](d/D)^{3/m} \quad (2)$$

where $S_{fs}$ and D now refer to the unitary stem and R is the two-piece to unitary strength ratio.

From Eq. 2, and FIGS. 6 and 7 one can design a two-piece stem of titanium alloy of similar materials with a fatigue strength of 85 ksi to be comparable in strength to a cast stem made of Cobalt-Chromium, which typically has a fatigue strength of about 35 ksi, by insuring that the stress concentration factor in the extension does not exceed 1.3. This is accomplished by setting radius B of the extension as equal to 0.25 times the extension diameter "$d_1$". Thus a Titanium two-piece stem can be made substantially equivalent, with respect to strength, to conventional Cobalt Chromium stems, which have been found to be relatively safe from fracture after decades of clinical use.

Since Titanium is more flexible than Cobalt Chromium alloy the bone into which a Titanium stem is implanted will carry more bending load than this bone would carry if a Cobalt chromium stem were implanted. Thus in general a Titanium stem will be exposed to lower bending loads than a Cobalt Chromium stem. Now in light of the fact that a properly designed Titanium alloy two-piece stem is as strong as a Cobalt Chromium stem but is exposed to lower bending loads it is clear that if Cobalt Chromium stems are safe with respect to fracture then a Titanium alloy two-piece stem must be safer still.

Figure 10:
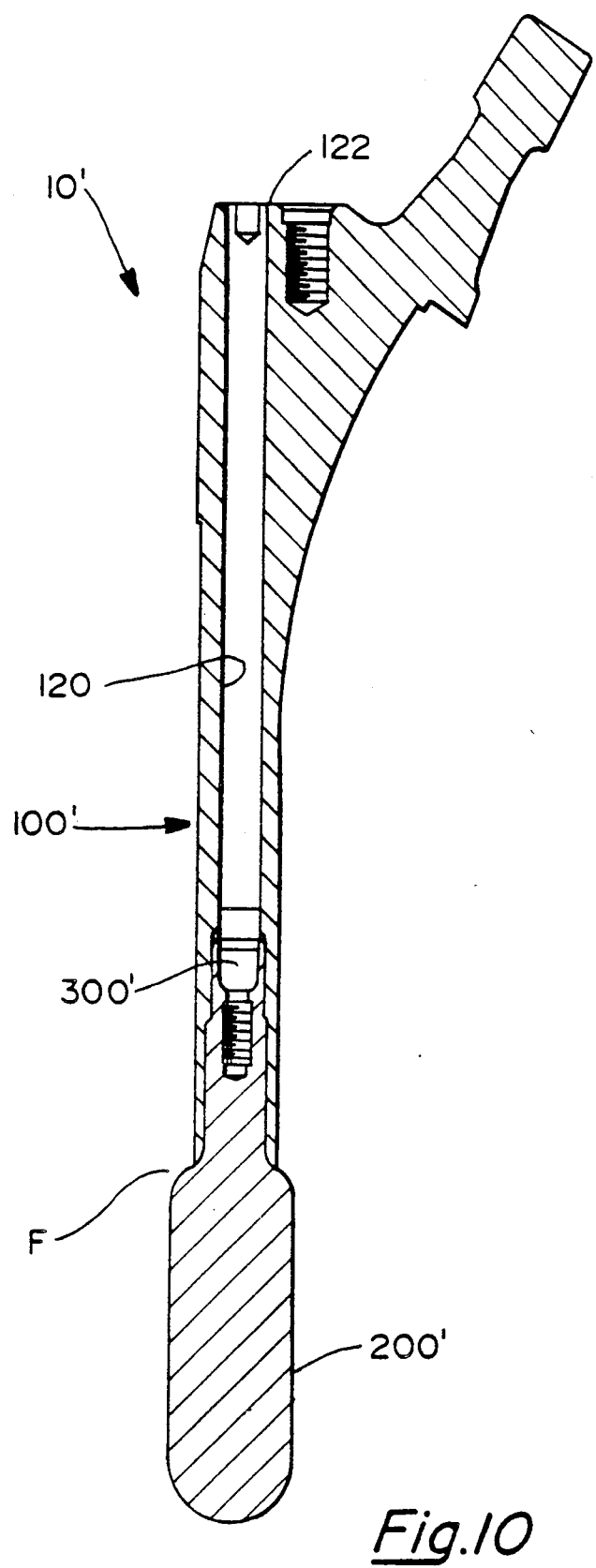
FIG. 10 is a cross sectional view similar to FIG. 7 but showing an alternate embodiment of the modular prothesis.

An alternate femoral prosthesis in accordance with the subject invention is identified generally by the numeral 10' in FIG. 10. The prosthesis 10' includes a stem 100', an extension 200' and a locking screw 300'. The slip fit interconnection between the stem 100' and the extension 200' may be similar to that described above and illustrated in FIGS. 1-7. However, unlike the preceding embodiment, the stem 100' is characterized by an aperture 120 extending entirely therethrough from a proximal surface region 122 to the distal end of the stem 100'. The aperture 120 is dimensioned to receive a locking screw 300' which threadedly engages the extension 200' to urge longitudinally extending segments 210 thereof outwardly into tight engagement with corresponding portions of the stem 100' as explained with respect to the previous embodiment. In the illustrated embodiment, the locking screw 300' is elongated and extends the entire distance from the extension 200' to the proximal surface region 122 of the stem 100'. Preferably the dimensions of the aperture 120 in the stem 100' are such that the locking screw 300' is loosely fit therein. In other embodiments, the locking screw 300' may be substantially shorter and may be accessed by an elongated tool (not shown) extending into the aperture 120.

The embodiment of the prosthesis 10' depicted in FIG. 10 has several significant advantages. For example, in some situations the condition of the patient may require a resection to surgically remove the entire modular prosthesis to enable replacement of at least a portion of the modular prosthesis. In embodiments where the extension of the prosthesis defines a larger diameter than the stem, as shown in FIG. 10, bone may grow into the region F at the interface of the small diameter stem 100' and large diameter extension 200'. This bone ingrowth could substantially complicate the removal of the prosthesis in embodiments where the locking screw is accessible only from the distal end of the extension. Although tools are available for removing ingrown bone, the presence of the elongated stem would make the use of such tools difficult at the relatively remote and obstructed interface of the distal end of the stem and the proximal end of the extension. The prosthesis 10' illustrated in FIG. 10 avoids these problems. In particular, the locking screw 300' can be accessed from the proximal surface region 122 of the prosthesis 10' to enable the locking screw 300' and the stem 100' to be separated from the extension 200' and removed from the femur of the patient. The removal of these portions of the system provides ready access to bone tissue that may have grown into engagement with the extension 200'. A threaded tool, similar to the locking screw 300', may then be engaged with the proximal end of the extension 200' to extract the extension 200' and thereby enable an alternate prosthesis to be surgically implanted.

Another advantage of the prosthesis illustrated in FIG. 10 relates to the aperture 120 passing entirely through the stem 100'. In particular, the aperture 120 can make the stem 100' substantially more flexible, thereby enabling a greater proportion of applied loads to be carried by the natural bone, as opposed to the prosthesis. By transferring a major portion of applied loads to the natural bone, bone disuse atrophy can be reduced substantially. The provision of the aperture 120 or other such longitudinally extending hollow center can be employed in prostheses that are of unitary construction, or other such nonmodular design, to increase the flexibility of the prosthesis and increase the proportion of the applied loads carried by the natural bone. For example, the stem of a nonmodular femoral prosthesis may include a longitudinally extending central hollow portion, such that a greater proportion of loads applied to the neck are transferred to the natural femur.

While the invention has been described with respect to a preferred embodiment, it will be apparent that various changes can be made without departing from the scope of the invention as defined by the appended claims. For example, the illustrated male and female components of the subject invention may be reversed in either illustrated embodiment. Additionally, in certain embodiments the female member of the prosthesis may be free of threads, with the threaded portion being disposed on internal surfaces of the flexible segments of the male component. A wedging action between the screw and the fingers can be achieved by employing a tapered screw and a correspondingly tapered array of threads on internal surfaces of the flexible segments. In still other embodiments, the flexible fingers may be provided with an inwardly formed groove which mates with an inwardly directed ridge on the female component of the system. These and other embodiments will be apparent to a person skilled in this art after having read this disclosure.

We claim:

1. A modular prosthesis comprising an elongated first component having a proximal end and a distal end and an aperture extending generally centrally therethrough from the proximal end to the distal end, a second component having a portion configured for engagement with the distal end of the first component and extending distally beyond the first component, a plurality of longitudinally extending flexible segments integral with one of the components, engaging means disposed on outwardly facing surface regions of the flexible segments for engaging the other of said components, and a locking screw disposed in the aperture and accessible from the proximal end of the first component and being threadedly engaged with one of said components and configured for securely urging the engaging means of the longitudinally extending flexible segments into engagement with the other of said components for lockingly retaining the second component in engagement with the distal end of the first component.

2. A modular prosthesis as in claim 1 wherein the first and second components are engaged in slip fit engagement.

3. A modular prosthesis as in claim 1 wherein the first component comprises inwardly facing engagement means for engaging the outwardly facing engagement means on the second component.

4. A modular prosthesis as in claim 1 wherein the locking screw comprises a shaft extending substantially from the second component to the proximal end of the first component.

5. A modular prosthesis as in claim 4 wherein portions of the locking screw passing through the aperture of the first component define smaller cross-sectional dimensions than the aperture in the first component, such that the first component is substantially hollow and is flexible in response to loads applied thereto.

6. A modular prosthesis as in claim 1 wherein the locking screw includes a tapered portion for urging selected portions of said components into engagement with one another.

7. A modular prosthesis as in claim 1 wherein portions of the second component distally of the first component define larger cross-sectional dimensions than portions of the first component adjacent thereto.

8. A modular femoral prosthesis comprising an elongated stem having a proximal end for disposition adjacent a proximal portion of a femur, said stem further having a distal end and an aperture extending centrally therethrough from the proximal end to the distal end, an extension having a proximal end and a distal end, the proximal end of the extension being engaged with the distal end of the stem, longitudinally extending flexible segments integral with a selected one of said stem and said extension, and a locking screw disposed at least adjacent the distal end of the stem and accessible from the proximal end of the stem through the aperture therein, said locking screw being dimensioned and configured to urge the flexible segments outwardly for lockingly engaging the stem with the extension.

9. A modular femoral prosthesis as in claim 8 wherein the distal end of the stem and the proximal end of the extension are disposed in slip fit engagement with one another.

10. A modular femoral prosthesis as in claim 8 wherein the locking screw comprises a shaft extending substantially the entire length of the stem such that an end of the shaft is adjacent the proximal end of the stem, said shaft defining a cross-sectional dimension less than the aperture in the stem, such that the stem is flexible independent of the shaft in response to loads applied to the stem.

* * * * *